(12) United States Patent
Yamamoto

(10) Patent No.: US 11,509,206 B2
(45) Date of Patent: Nov. 22, 2022

(54) LINEAR-MOTOR TYPE TRANSPORT DEVICE FOR TRANSPORTING MATERIAL FOR ABSORBENT ARTICLE AND METHOD FOR MANUFACTURING ABSORBENT ARTICLE

(71) Applicant: UNICHARM Corporation, Ehime (JP)

(72) Inventor: Hiroki Yamamoto, Kagawa (JP)

(73) Assignee: Unicharm Corporation, Ehime (JP)

( * ) Notice: Subject to any disclaimer, the term of this patent is extended or adjusted under 35 U.S.C. 154(b) by 127 days.

(21) Appl. No.: 17/062,051

(22) Filed: Oct. 2, 2020

(65) Prior Publication Data
US 2021/0104944 A1    Apr. 8, 2021

(30) Foreign Application Priority Data

Oct. 3, 2019   (JP) .............................. JP2019-183042

(51) Int. Cl.
*H02K 41/03*    (2006.01)
*H02K 7/06*    (2006.01)
(Continued)

(52) U.S. Cl.
CPC ............. *H02K 41/031* (2013.01); *H02K 7/06* (2013.01); *H02P 6/006* (2013.01); *H02K 16/00* (2013.01)

(58) Field of Classification Search
CPC ...... H02K 41/031; H02K 41/03; H02K 41/00; H02K 7/06; H02K 16/02; H02K 16/00;
(Continued)

(56) References Cited

U.S. PATENT DOCUMENTS

2002/0125105 A1\* 9/2002 Nakakado ............ B65G 47/848
                                                         198/471.1
2003/0230941 A1\* 12/2003 Jacobs ................. B65G 47/841
                                                         310/12.19
(Continued)

FOREIGN PATENT DOCUMENTS

WO    2018/037304 A1    3/2018
WO    2019/150297 A1    8/2019

OTHER PUBLICATIONS

Office Action issued in counterpart European Patent Application No. 20198477.0 dated Mar. 12, 2021 (10 pages).

*Primary Examiner* — Michael Andrews
(74) *Attorney, Agent, or Firm* — Osha Bergman Watanabe & Burton LLP

(57) ABSTRACT

A linear-motor type transport device for transporting material for an absorbent article includes: a shaft portion that has an axial direction, a radial direction, and a circumferential direction; a pair of guide portions that is disposed on the shaft portion with a predetermined axial-direction space between the guide portions and that forms an orbital transport path that extends along the circumferential direction; a mobile unit that moves on the transport path along the guide portions while supporting a transport head rotatably about a rotation axis; a cam mechanism that rotates the transport head about the rotation axis through a predetermined angle when the mobile unit is moved on the transport path; and a controller that moves the mobile unit by supplying currents to conductors and generating a propulsive force between one of the conductors and a magnet that is disposed on the mobile unit.

9 Claims, 12 Drawing Sheets

(51) Int. Cl.
*H02P 6/00* (2016.01)
*H02K 16/00* (2006.01)

(58) Field of Classification Search
CPC ............... H02P 6/006; A61F 13/15764; A61F 13/115577; A61F 2013/15821
USPC ................................ 310/12.01, 12.04, 12.11
See application file for complete search history.

(56) References Cited

U.S. PATENT DOCUMENTS

| | | | |
|---|---|---|---|
| 2008/0289468 A1* | 11/2008 | Nakakado | B65H 35/08 83/267 |
| 2016/0164395 A1* | 6/2016 | Sommerhalter, Jr. | B60L 13/03 310/12.11 |
| 2016/0376110 A1* | 12/2016 | Schneider | B65G 47/244 198/377.02 |
| 2019/0060134 A1 | 2/2019 | Piantoni et al. | |
| 2021/0101762 A1* | 4/2021 | Tordini | B65H 35/08 |

* cited by examiner

LINEAR-MOTOR TYPE TRANSPORT DEVICE FOR TRANSPORTING MATERIAL FOR ABSORBENT ARTICLE AND METHOD FOR MANUFACTURING ABSORBENT ARTICLE

CROSS-REFERENCE TO RELATED APPLICATION

The present application claims priority pursuant to 35 U.S.C. § 119 from Japanese patent application No. 2019-183042, filed on Oct. 3, 2019, the entire disclosure of which is hereby incorporated herein by reference.

BACKGROUND

Technical Field

The present invention relates to a linear-motor type transport device for transporting material for an absorbent article and a method for manufacturing an absorbent article.

Related Art

In relation to manufacturing of absorbent articles such as disposable diapers and sanitary napkins, a transport device has been proposed which can increase the efficiency in manufacturing the absorbent articles by efficiently transporting materials for the absorbent articles. For example, WO2018/037304A1 discloses a transport device (7) in which an object (3) is transferred with a holding head (10) on an annular transfer path (T), the holding head (10) supporting a holding element (11) that is capable of rotating about a second rotation axis (R2), the holding head (10) being slidable along a pair of annular guides (15, 35). In the disclosed transport device (7), the object (3), namely a material to be transported, is moved (transported) on the annular transfer path (T) while being supported by the holding element (11) and rotating about the second rotation axis (R2). As a result, an efficient transport operation is realized.

The transport device disclosed in WO2018/037304A1 includes: a drive mechanism for moving the holding head (mobile unit) along a pair of guide portions; and a cam mechanism for rotating the holding element about the rotation axis. However, it has been difficult to dispose all of those mechanisms (the drive mechanism and the cam mechanism) between the pair of guide portions due to space limitations of the transport device. In other words, at least part of the drive mechanism and the cam mechanism has needed to be disposed outward (on the one side) with respect to the pair of guide portions. In the case of WO2018/037304A1, for example, the cam mechanism is disposed between the pair of guide portions, whereas the drive mechanism is disposed on a side outward (on the one side) with respect to the pair of guide portions.

In the above-described transport device, there is a risk that a rotational force generated from the cam mechanism during rotation of a transport head and a force generated due to acceleration or deceleration when a mobile unit is driven by the drive mechanism generate moments of different magnitudes acting on each of the pair of guide portions. For example, when the drive mechanism is disposed outward (on the one side) with respect to the pair of guide portions, moments of different magnitudes act on the one-side guide portion and the other-side guide portion. This increases moment loads applied to the guide portions. Accordingly, there are risks that the mobile unit is difficult to stably operate (move), and that durability degrades due to wear of the guide portions. In particular, in the case of transporting the materials for the absorbent articles, which is assumed to be manufactured in a mass production system, the above-mentioned issue is more likely to appear with an increase in transport velocity.

SUMMARY

One or more embodiments of the present invention, in a transport device transporting a to-be-transported object by moving a mobile unit along a pair of guide portions, reduce moment loads acting on the guide portions.

According to one or more embodiments, a linear-motor type transport device for transporting material for an absorbent article includes:
a shaft portion having an axial direction, a radial direction, and a circumferential direction,
    the shaft portion being supported such that the axial direction extends horizontally from a vertically erected wall;
a pair of guide portions disposed on the shaft portion with a predetermined axial-direction space between the pair of guide portions,
    the pair of guide portions forming an orbital transport path that extends along the circumferential direction;
a mobile unit that moves on the transport path along the guide portions while supporting a transport head rotatably about a rotation axis,
    the rotation axis extending along the radial direction,
    the transport head transporting a material for an absorbent article;
a cam mechanism that rotates the transport head about the rotation axis through a predetermined angle when the mobile unit is moved on the transport path; and
a control unit (i.e., controller) that moves the mobile unit,
    the moving being performed by supplying currents to a plurality of conductors and generating a propulsive force between the conductor and a magnet that is disposed on the mobile unit,
    the plurality of conductors being disposed along the transport path,
    the cam mechanism and the magnet being arranged between the pair of guide portions in the axial direction.

DETAILED DESCRIPTION

Figure 1:
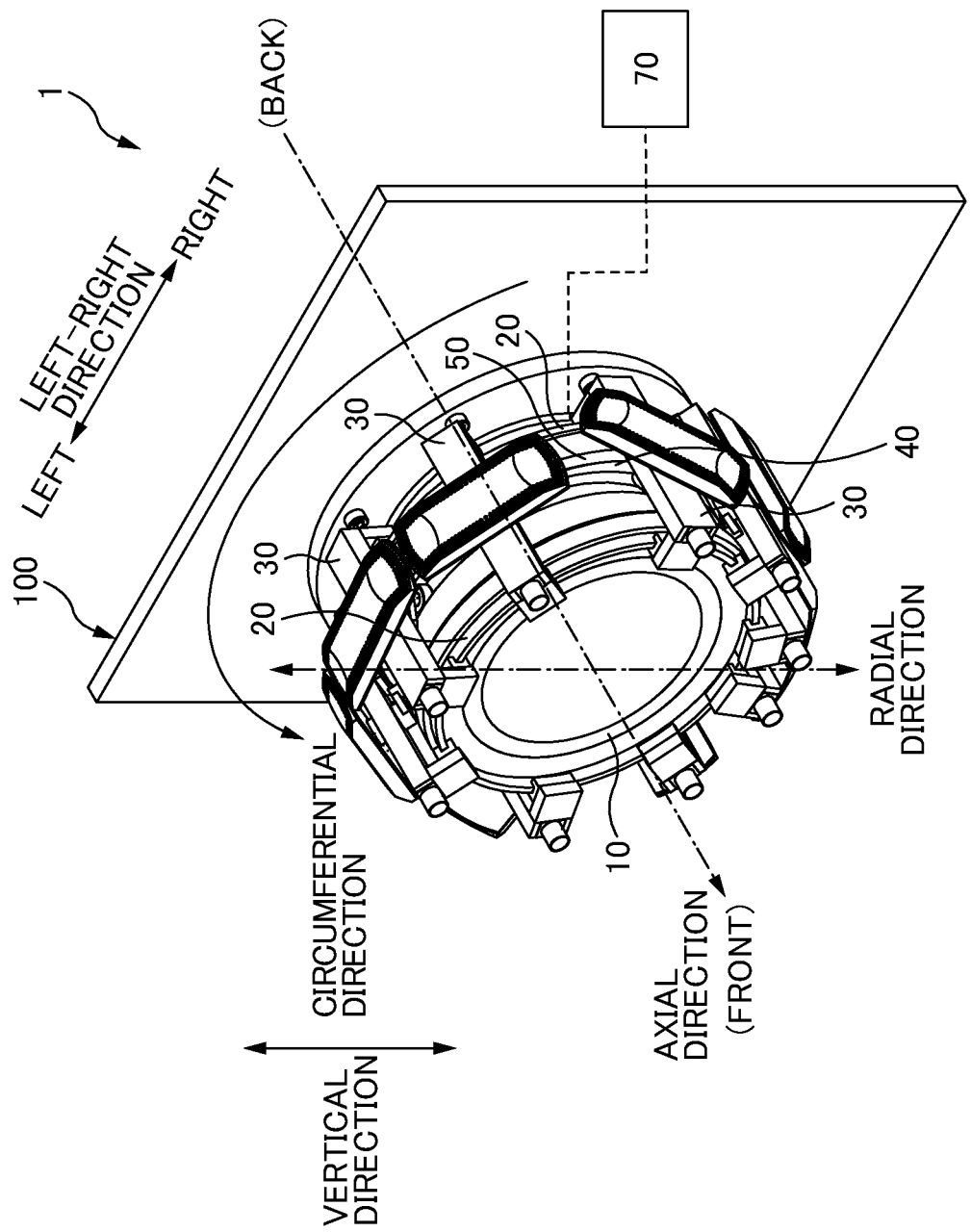
FIG. 1 is a perspective view illustrating the entire structure of a transport device 1 according to a first embodiment.

Embodiments of the present invention will be described herein with reference to the drawings. Those skilled in the art will recognize that many alternative embodiments can be accomplished using the teaching of the present invention and that the present invention is not limited to the embodiments illustrated herein for explanatory purposes.

A linear-motor type transport device for transporting material for an absorbent article includes:

a shaft portion having an axial direction, a radial direction, and a circumferential direction,
   the shaft portion being supported such that the axial direction extends horizontally from a vertically erected wall;
a pair of guide portions disposed on the shaft portion with a predetermined axial-direction space between the pair of guide portions,
   the pair of guide portions forming an orbital transport path that extends along the circumferential direction;
a mobile unit that moves on the transport path along the guide portions while supporting a transport head rotatably about a rotation axis,
   the rotation axis extending along the radial direction,
   the transport head transporting a material for an absorbent article;
a cam mechanism that rotates the transport head about the rotation axis through a predetermined angle when the mobile unit is moved on the transport path; and
   a control unit that moves the mobile unit,
   the moving being performed by supplying currents to a plurality of conductors and generating a propulsive force between the conductor and a magnet that is disposed on the mobile unit,
   the plurality of conductors being disposed along the transport path,
   the cam mechanism and the magnet being arranged between the pair of guide portions in the axial direction.

According to the above-described linear-motor type transport device for transporting material for an absorbent article, in comparison with the case in which various components, such as the conductor and the magnet for driving the mobile unit and the cam mechanism for rotating the transport head, are disposed on an outer side (only one side) of the pair of guide portions, differences in distances from the pair of guide portions to the various components are reduced. As a result, moment loads acting on the pair of guide portions are reduced, durability of the pair of guide portions is increased, and an operation of moving the mobile unit can be stabilized more easily.

A linear-motor type transport device for transporting material for an absorbent article includes:

a shaft portion having an axial direction, a radial direction, and a circumferential direction,
   the shaft portion being supported such that the axial direction extends horizontally from a vertically erected wall;
a pair of guide portions disposed on the shaft portion with a predetermined axial-direction space between the pair of guide portions,
   the pair of guide portions forming an orbital transport path that extends along the circumferential direction;
a mobile unit that moves on the transport path along the guide portions while supporting a transport head rotatably about a rotation axis,
   the rotation axis extending along the radial direction,
   the transport head transporting a material for an absorbent article;
a cam mechanism that rotates the transport head about the rotation axis through a predetermined angle when the mobile unit is moved on the transport path; and
   a control unit that moves the mobile unit,
   the moving being performed by supplying currents to a plurality of conductors and generating a propulsive force between the conductor and a magnet that is disposed on the mobile unit,
   the plurality of conductors being disposed along the transport path,
   the pair of guide portions including a first guide portion and a second guide portion,
   the first guide portion being disposed on one side in the axial direction with respect to the wall,
   the second guide portion being disposed on the one side in the axial direction with respect to the first guide portion,
   the cam mechanism being disposed between the first guide portion and the second guide portion in the axial direction,
   the magnet being disposed at each of positions,
   one of the positions being located on the one side in the axial direction with respect to the wall and on another side in the axial direction with respect to the first guide portion,
   another one of the positions being located on the one side in the axial direction with respect to the second guide portion.

According to the above-described linear-motor type transport device for transporting material for an absorbent article, in comparison with the case in which various components, such as the conductor and the magnet for driving the mobile unit and the cam mechanism for rotating the transport head, are disposed on an outer side (only one side) of the pair of guide portions, differences in distances from the pair of guide portions to the various components are reduced. As a result, moment loads acting on the pair of guide portions are reduced, durability of the pair of guide portions is increased, and an operation of moving the mobile unit can be stabilized more easily.

In one or more embodiments, the guide portions are capable of moving rotationally in the circumferential direction.

According to the above-described linear-motor type transport device for transporting material for an absorbent article, compared with the case where the guide portions are not moved in the circumferential direction, when the mobile unit is driven to rotate in the circumferential direction at a predetermined angular velocity, it is possible to decrease a relative velocity of the mobile unit to the guide portions.

This reduces frictional resistance between the mobile unit and each of the guide portions, making it possible to increase the durability of the guide portions.

In one or more embodiments, the conductors are driven to rotate in the circumferential direction.

According to the above-described linear-motor type transport device for transporting material for an absorbent article, when the mobile unit is driven to rotate in the circumferential direction at the predetermined angular velocity, a relative velocity of the mobile unit to the conductor can be made lower than when the conductor is not moved in the circumferential direction. This makes the control unit easier to control of a current supplied to the conductor, making it possible to more easily stabilize the operation of moving the mobile unit.

In one or more embodiments, the conductors are driven to rotate in the circumferential direction together with at least one of the pair of guide portions.

According to the above-described linear-motor type transport device for transporting material for an absorbent article, compared with the case where the conductor and the guide portion are not moved in the circumferential direction, when the mobile unit is driven to rotate in the circumferential direction at the predetermined angular velocity, it is possible to decrease the relative velocities of the mobile unit to the conductor and to the at least one guide portion. As a result, the operation of moving the mobile unit is stabilized more easily, and the durability of the guide portion can be increased.

In one or more embodiments, the pair of guide portions includes a first guide portion and a second guide portion, the first guide portion being disposed on one side in the axial direction with respect to the wall, the second guide portion being disposed on the one side in the axial direction with respect to the first guide portion, and a drive mechanism is disposed between the first guide portion and the wall, the drive mechanism being for driving and rotating the conductors and the guide portions.

According to the above-described linear-motor type transport device for transporting material for an absorbent article, the drive mechanism can be disposed in a narrow space between the wall and the first guide portion. The drive mechanism can drive and rotate the first guide portion, also making it possible to simultaneously perform input of a driving force to drive and rotate the mobile unit. It is hence possible to form the entirety of the transport device in a compact size, and to increase the degree of freedom in design while minimizing a space for installation of the transport mechanism.

In one or more embodiments, one of the pair of guide portions is driven to rotate in the circumferential direction together with the conductors, and another one of the pair of guide portions is capable of freely moving rotationally in the circumferential direction.

According to the above-described linear-motor type transport device for transporting material for an absorbent article, the control unit is just required to control the rotational operation for only one of the pair of guide portions and is not required to control the rotational operation for the other guide portion. As a result, the entirety of the transport device can be controlled more easily.

In one or more embodiments, both of the pair of guide portions are driven to rotate in the circumferential direction together with the conductors.

According to the above-described linear-motor type transport device for transporting material for an absorbent article, since the pair of guide portions can be both driven and rotated, frictional resistance between the guide portions and the mobile unit can be further reduced. In addition, since the pair of conductors are also driven and rotated together with the guide portions, the operation of the mobile unit can be further stabilized more easily.

In one or more embodiments, in the axial direction, a distance from a middle position between the pair of guide portions to the cam mechanism is smaller than a distance from the middle position to the conductor.

According to the above-described linear-motor type transport device for transporting material for an absorbent article, the cam mechanism is disposed as close as possible to the middle position between the first guide portion and the second guide portion in the axial direction. Accordingly, a force generated during the operation of rotating the transport head is more likely to be evenly distributed to the first guide portion and the second guide portion. As a result, the moment loads acting on the guide portions can be further reduced more easily.

A method for manufacturing an absorbent article using a material for an absorbent article, the material being transported in a direction of transport by the above-described linear-motor type transport device.

According to the above-described method for manufacturing an absorbent article, in a process of manufacturing the absorbent article such as a disposable diaper, a direction of attachment of an absorbent body can be adjusted while the absorbent body is being transported. Hence the absorbent article can be manufactured efficiently.

First Embodiment

Structure of Transport Device for Transporting Material for Absorbent Article

Figure 2A:
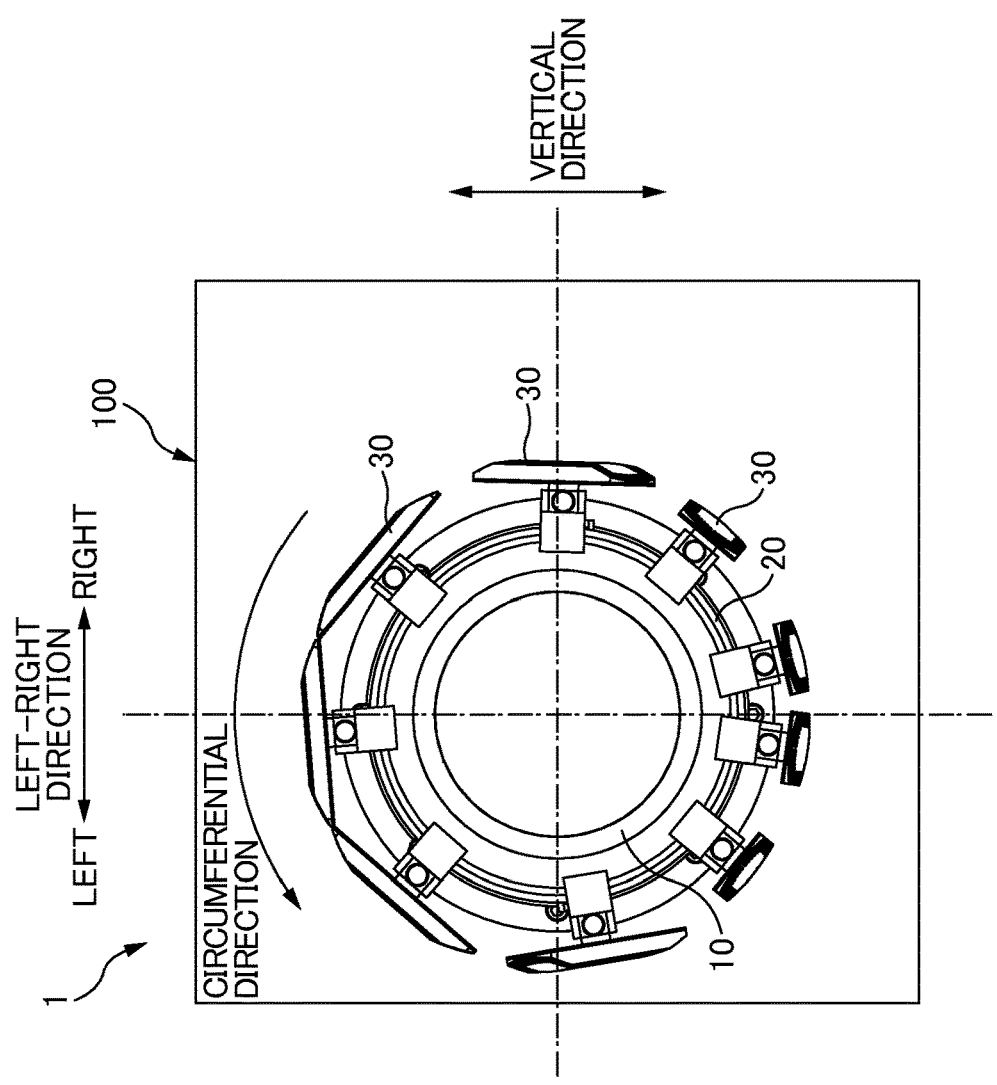
FIG. 2A is a plan view of the transport device 1 when viewed from the front side (one side) in the axial direction.
Figure 2B:
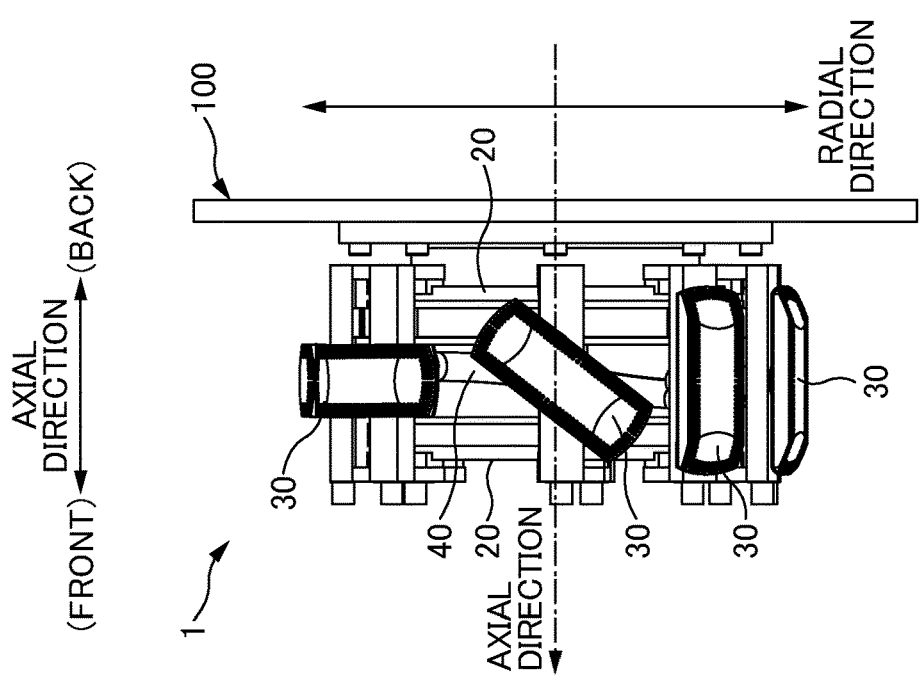
FIG. 2B is a side view of the transport device 1 illustrated in FIG. 2A when viewed from the one side in the left-right direction.
Figure 3:
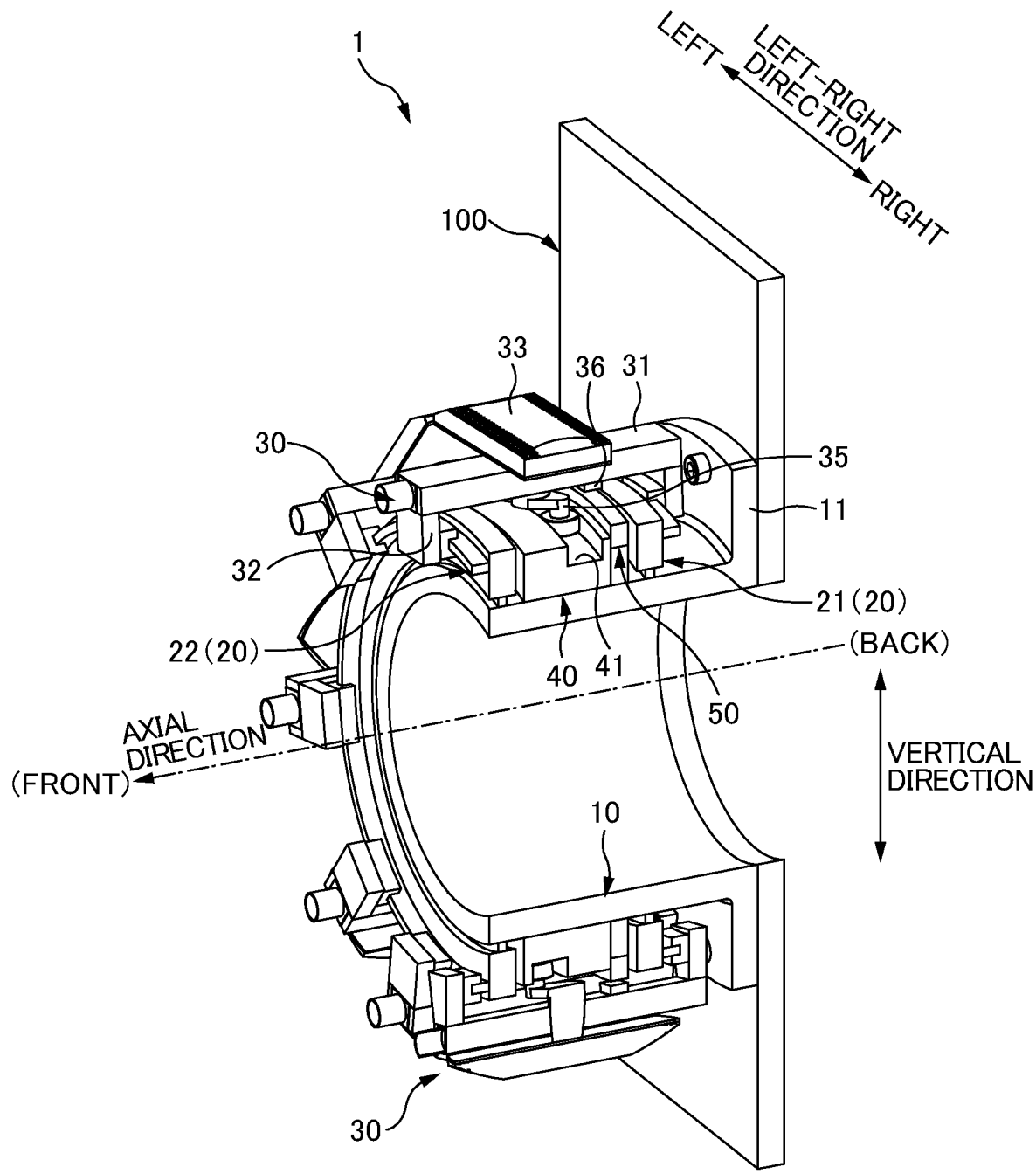
FIG. 3 is a sectional perspective view illustrating an inner structure of the transport device 1.
Figure 4:
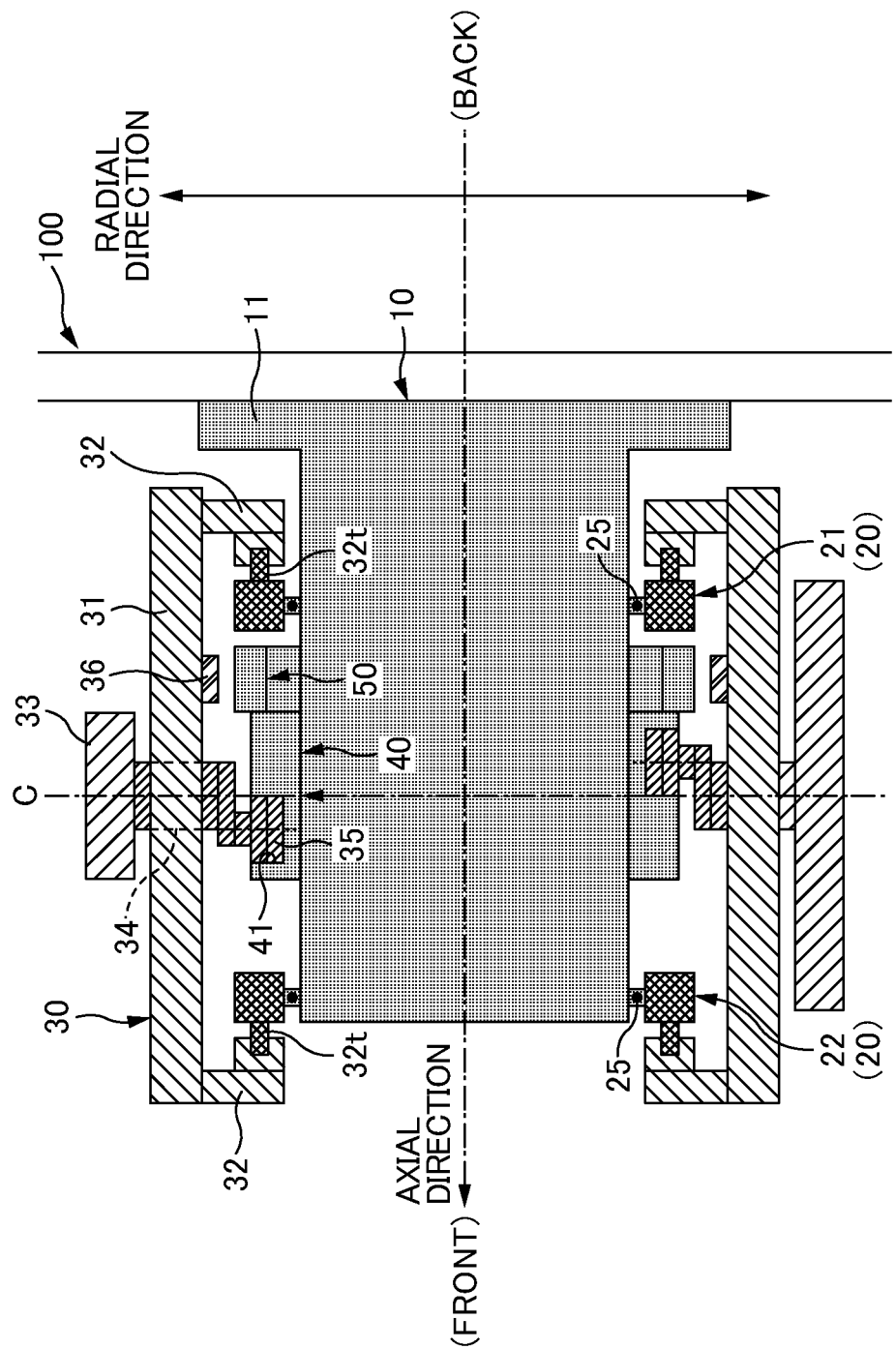
FIG. 4 is a schematic sectional view of the transport device 1.

A first embodiment is described in connection with a transport device 1 for transporting material for an absorbent article (hereinafter also simply called a "transport device 1") that transports materials (for example, an absorbent body) for absorbent articles such as diapers and napkins. FIG. 1 is a perspective view of an entire structure of the transport device 1 according to the first embodiment. The transport device 1 includes a shaft portion 10, guide portions 20, mobile units 30, a cam mechanism 40, conductors 50, and a control unit 70. The transport device 1 is fixed to a wall 100 that is erected vertically (in a vertical direction in FIG. 1) from a horizontal surface such as a ground surface or a surface plate. The transport device 1 has an axial direction, a radial direction, and a circumferential direction defined as per illustrated in FIG. 1. In the following description, with respect to the wall 100, the side where the transport device 1 is installed is assumed to be a front side (one side) in the axial direction, and the opposite side is assumed to be a back side (other side) in the axial direction. FIG. 2A is a plan view of the transport device 1 when viewed from the front side (one side) in the axial direction, and FIG. 2B is a side view of the transport device 1 illustrated in FIG. 2A when viewed from the one side (right side) in a left-right direction. FIG. 3 is a sectional perspective view illustrating an inner structure of the transport device 1. FIG. 4 is a schematic sectional view of the transport device 1.

The shaft portion 10 is constituted by a column having a substantially circular hollow or solid cylindrical shape and supporting the guide portions 20 and the cam mechanism 40.

The shaft portion 10 is fixed to and supported by the wall 100 so that its center axis extends along the axial direction. In one or more embodiments, a flange surface 11 is formed in an other-side end of the shaft portion 10 in the axial direction, and the shaft portion 10 is fixed to the wall 100 with the flange surface 11. In other words, the shaft portion 10 is supported such that the axial direction extends horizontally from the wall 100.

The guide portions 20 are guide rails for regulating a direction of movement of the mobile unit 30 and are provided in a pair on an outer circumferential surface of the shaft portion 10 with a predetermined axial-direction space between the pair of guide portions. In one or more embodiments, of the pair of guide portions 20, the one disposed on the back side (other side) in the axial direction, is called a first guide portion 21, and the other guide portion disposed on the front side (one side) in the axial direction is called a second guide portion 22 (see FIGS. 3 and 4). More specifically, in the axial direction, the first guide portion 21 is disposed on the front side (one side) with respect to the wall 100, and the second guide portion 22 is disposed on the front side (one side) with respect to the first guide portion 21. The first guide portion 21 and the second guide portion 22 are each constituted in the form of a ring extending in the circumferential direction along the outer circumferential surface of the shaft portion 10, forming an orbital transport path extending along the circumferential direction of the shaft portion 10.

As illustrated in FIG. 4, in one or more embodiments, ball bearings 25 are disposed between the guide portions 20 and the outer circumferential surface of the shaft portion 10. With the presence of the ball bearings 25, the guide portions 20 can move rotationally in the circumferential direction on the outer circumferential surface of the shaft portion 10. However, the guide portions 20 are not always required to be rotationally movable with respect to the shaft portion 10, and the guide portions 20 may be immovably fixed to the shaft portion 10.

Figure 5:
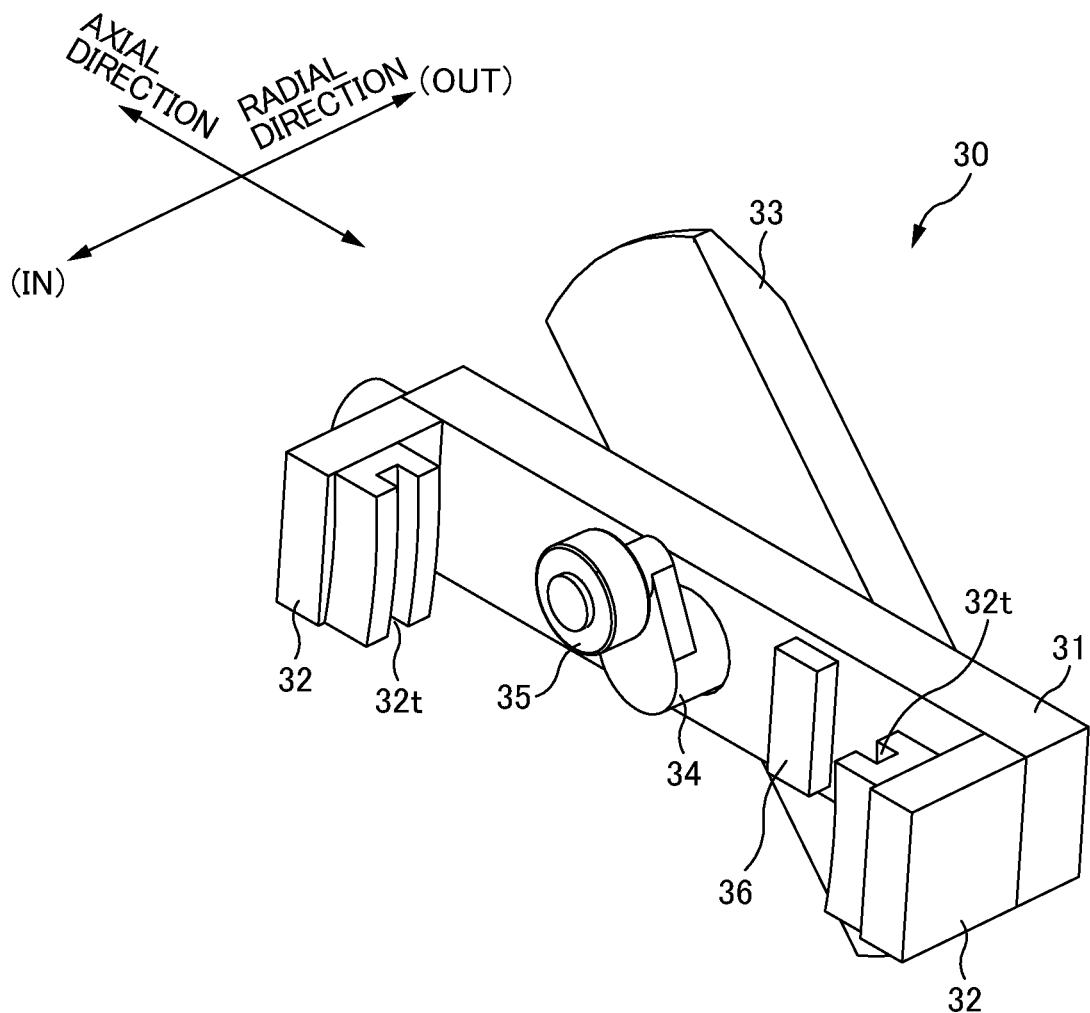
FIG. 5 is a schematic perspective view illustrating a structure of a mobile unit 30.

FIG. 5 is a schematic perspective view illustrating a structure of the mobile unit 30. The mobile unit 30 is moved on the transport path along the guide portions 20, thereby moving the material for the absorbent article in a direction of transport. The mobile unit 30 includes a main body portion 31, slide portions 32, a transport head 33, a transport-head connection shaft 34, a cam follower 35, and a magnet 36.

The main body portion 31 is an axially elongated member in the shape of a substantially rectangular parallelepiped, and supports the above-mentioned parts, namely from the slide portions 32 to the magnet 36. The slide portions 32 are disposed in a pair at two axial-direction ends of the main body portion 31, and each slide portion 32 has a groove 32t extending in a direction perpendicular to both the radial direction and the axial direction in FIG. 5 (namely, a direction corresponding to the circumferential direction in FIG. 1). As illustrated in FIG. 4, the grooves 32t are engaged with the guide portions 20 (the first guide portion 21 and the second guide portion 22) in a slidable manner. As a result, the mobile units 30 are attached to the guide portions 20 such that the mobile units 30 are slidable on the transport path along the guide portions 20.

The transport head 33 holds the material (for example, the absorbent body) for the absorbent article, namely, a to-be-transported material, and is disposed on the outer side of the main body portion 31 in the radial direction. In one or more embodiments, a suction mechanism (not illustrated) is provided on a surface of the transport head 33 (outer surface in the radial direction) so as to be capable of sucking and holding the to-be-transported material (material such as the absorbent body). Furthermore, the transport head 33 is connected to a substantially axial-direction central region of the main body portion 31 by the transport-head connection shaft 34. The transport-head connection shaft 34 is a shaft member arranged extending along the radial direction of the transport device 1, and the shaft 34 is disposed to be rotatable about an axis along the radial direction, with respect to the main body portion 31. As illustrated in FIG. 4, the radial-direction outer end of the transport-head connection shaft 34 is coupled to the transport head 33, and the radial-direction inner end of the transport-head connection shaft 34 is coupled to the cam follower 35. In other words, the transport head 33 and the cam follower 35 are coupled integrally with each other through the transport-head connection shaft 34 and are attached to the main body portion 31 so as to be rotatable about the axis of the radial direction in such a manner that the transport-head connection shaft 34 serves as a rotation axis.

The cam follower 35 is a member for rotating the transport head 33 about the rotation axis extending in the radial direction and is disposed on the inner side of the main body portion 31 in the radial direction (namely, on the opposite side to the transport head 33 with respect to the main body portion 31). As illustrated in FIG. 4, the cam follower 35 is positioned eccentric to an axial center of the transport-head connection shaft 34 (namely, the rotation axis of the transport head 33) by a predetermined distance in the axial direction of the shaft portion 10. As the cam follower 35 follows the shape of a cam groove 41 of the cam mechanism 40 described below, the transport head 33 (and the transport-head connection shaft 34) is rotated about the rotation axis through a predetermined angle.

The magnet 36 is a permanent magnet and is disposed on an inner surface of the main body portion 31 in the radial direction so as to be positioned opposite to the conductor 50 (described later) in the radial direction (see FIG. 4).

The mobile unit 30 may have a position detector (for example, a linear encoder) (not illustrated) such that position information of the mobile unit 30 on the transport path can be transmitted to the control unit 70.

The cam mechanism 40 is a so-called cylindrical cam formed continuously on the outer circumferential surface of the shaft portion 10 along the circumferential direction. The cam mechanism 40 has the cam groove 41 that corresponds to a cam driver. The axial-direction position of the cam groove 41 varies depending on the circumferential-direction position of the cam groove 41. In other words, the cam groove 41 is formed in a shape curving along the circumferential direction. Accordingly, as the mobile unit 30 moves on the transport path along the circumferential direction, the axial-direction position of the cam follower 35 varies following the shape of the cam groove 41, thus causing the transport head 33 to rotate about the axis of the radial direction through the transport-head connection shaft 34. In FIGS. 1 and 2, for each of predetermined circumferential-direction positions of the transport device 1, each transport head 33 is illustrated in a state rotated about the axis along the radial direction through a predetermined angle.

In one or more embodiments, the cam mechanism 40 is adjusted such that each of the transport heads 33 (the mobile units 30) rotates 90 degrees about the axis of the radial direction while running around the transport path one time. This enables a transport operation as follow: receiving the to-be-transported material (for example, the material for the absorbent article) at a predetermined position on the transport path; then changing its state to a state in which the object has been rotated 90 degrees; and finally, at another position on the transport path, delivering the object to a next step. For example, in the case of transporting a substantially rectangular absorbent body as the material for the absorbent article (for example, a disposable diaper), the absorbent body transported from a production line of the absorbent body is received by the transport device 1, is rotated 90 degrees in orientation of a lengthwise direction thereof, and is then delivered to a next step (for example, a step of transferring the absorbent body to a diaper outer covering material). Thus, in a production process of the absorbent article (disposable diaper), a direction of attachment of the absorbent body can be adjusted while the absorbent body is being transported. As a result, the absorbent article can be manufactured efficiently.

The conductor 50 is a coil generating a magnetic field with a supply of a current, and multiple conductors are disposed on the outer circumferential surface of the shaft portion 10 along the circumferential direction. Controlling the currents supplied to the conductors 50 makes it possible to change magnetic poles of the conductors 50 successively along the circumferential direction. Accordingly, a propulsive force (attractive force and repulsive force) can be generated between the conductor 50 and the magnet 36 of the mobile unit 30, making it possible to propel the mobile unit 30 in the direction of transport in accordance with the principle of a linear motor. In other words, the conductor 50 functions as a stator of the linear motor.

By controlling the currents supplied to the conductors 50, the control unit 70 moves or stops the multiple mobile units 30 disposed on the transport path in the direction of transport, thereby controlling the positions and movement velocities of the individual mobile units 30.

Operation of Transport Device 1

The operation of the transport device 1 in the case of transporting the to-be-transported material (material for the absorbent article) will be described below. In the transport device 1, as described above, the mobile unit 30 is moved on the transport path along the pair of guide portions 21 and 22 in the circumferential direction, in such a state that the to-be-transported material is held on the transport head 33. During the movement of the mobile unit 30, the transport head 33 is rotated by the cam mechanism 40 in the radial direction through the predetermined angle (for example, 90 degrees) to change the orientation of the object while the to-be-transported material is transported. In the transport device 1, not only the cam mechanism 40 for rotating the transport head 33, but also the conductor 50 and the magnet 36 for inputting a driving force to move the mobile unit 30 are disposed between the pair of guide portions 21 and 22 in the axial direction. Therefore, moment loads acting on the pair of guide portions 21 and 22 can be reduced compared with those in a related-art transport device. The principle of causing the above-mentioned result will be described below.

Figure 6A:
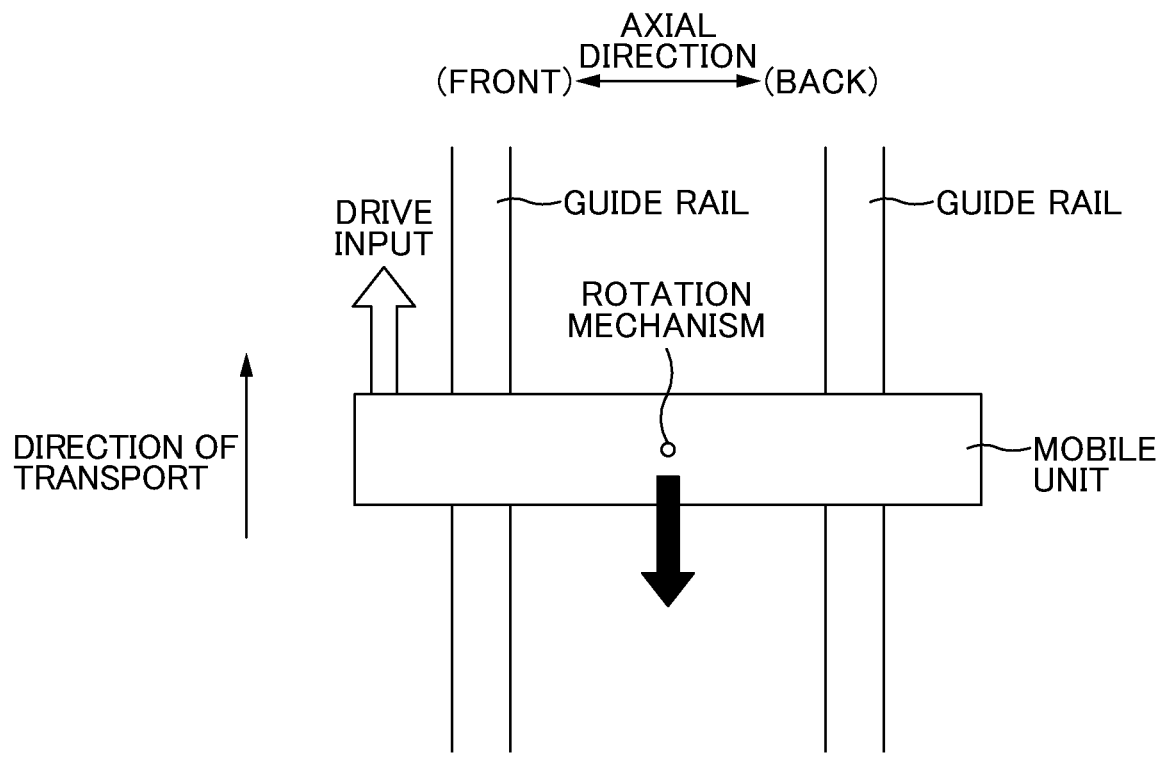
FIG. 6A is an explanatory view illustrating a relation between forces acting during transport in a related-art transport device.
Figure 6B:
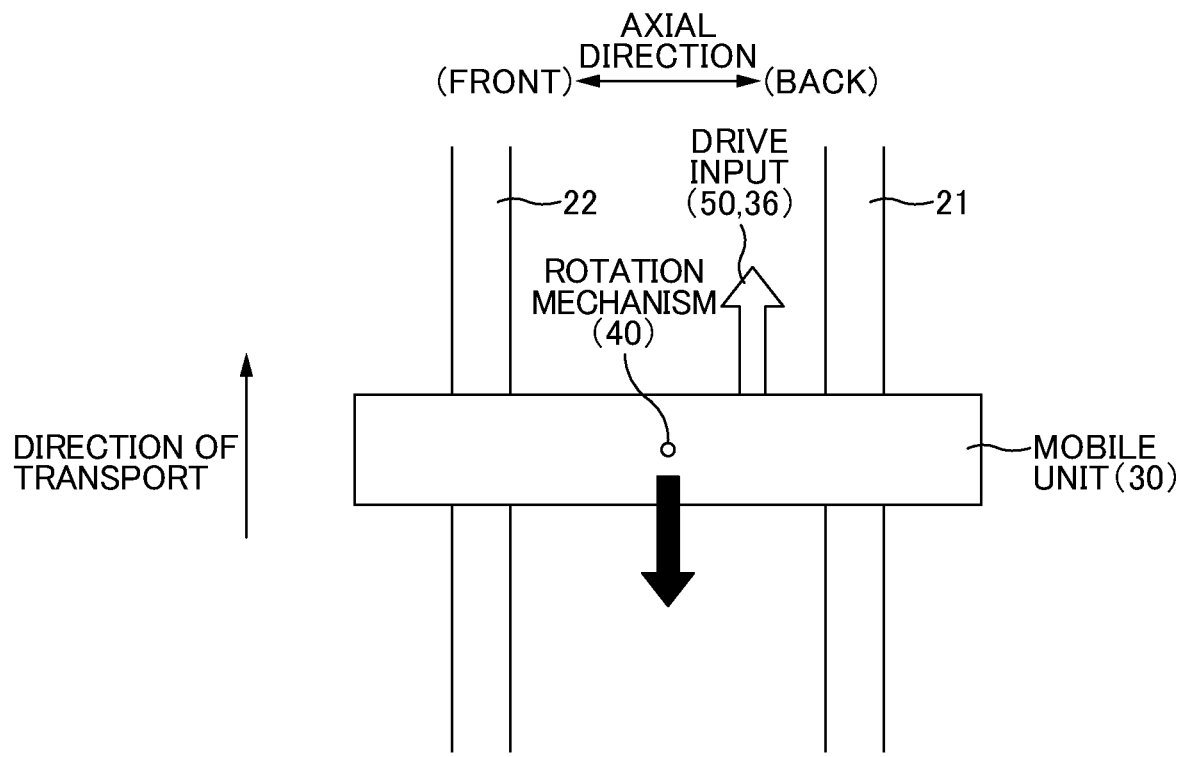
FIG. 6B is an explanatory view illustrating a relation between forces acting during transport in the transport device 1 according to the first embodiment.

FIG. 6A is an explanatory view illustrating a relation between forces acting during transport in the related-art transport device. FIG. 6B is an explanatory view illustrating a relation between forces acting during transport in the transport device 1 according to the first embodiment.

There is assumed a related-art transport device including a mobile unit (corresponding to the mobile unit 30 of the transport device 1) that is disposed so as to bridge a pair of guide rails (corresponding to the guide portions 20 of the transport device 1). It is assumed that this transport device includes: a rotation mechanism (corresponding to the cam mechanism 40 of the transport device 1) for rotating a transport head; and a drive input unit (for example, a servomotor) for accelerating and decelerating the mobile unit to control movement of the transport head. In this case, at least either one of the rotation mechanism and the drive input unit needs to be disposed on the outer side of the pair of guide rails in the axial direction. In the example illustrated in FIG. 6A, the rotation mechanism is disposed between the pair of guide rails in the axial direction, and the drive input unit is disposed outward (front side in the axial direction) with respect to the pair of guide rails. Alternatively, when the drive input unit is disposed between the pair of guide rails, the rotation mechanism is disposed outward with respect to the pair of guide rails. The reason is that, in the general transport device of the related art, a space between the pair of guide rails is restricted and hence it is impossible to ensure a space sufficient to install both the cam mechanism and the drive input unit between the pair of guide rails.

In the above-described case, among the pair of guide rails, different moment loads act on the guide rail positioned closer to the drive input unit (on the front side in the axial direction in FIG. 6A) and on the other guide rail positioned farther away from the drive input unit (on the back side in the axial direction in FIG. 6A). This gives rise to an issue that the durability of the pair of guide rails is apt to degrade and a difficulty arises in stably moving the mobile unit.

In contrast, in the transport device 1 according to one or more embodiments, as illustrated in FIG. 6B, not only the cam mechanism 40 for rotating the transport head 33, but also the conductor 50 and the magnet 36 for inputting the driving force to move the mobile unit 30 are disposed between the pair of guide portions 21 and 22 in the axial direction. With such an arrangement, a difference in distances from the drive input unit (including the conductor 50 and the magnet 36) to the pair of guide portions 21 and 22 in the axial direction is reduced in comparison with that in the related art illustrated in FIG. 6A. Accordingly, the moment loads acting on the pair of guide portions 21 and 22 are reduced and the durability of the pair of guide portions 21 and 22 is increased. In addition, the operation of moving the mobile unit 30 is easier to stabilize.

Furthermore, in the transport device 1 according to one or more embodiments, the pair of guide portions 21 and 22 are mounted to the outer circumferential surface of the shaft portion 10 with the ball bearings 25 interposed therebetween. In other words, the pair of guide portions 21 and 22 are disposed in a movable state in the circumferential direction. Accordingly, in the transport operation by the transport device 1, as the mobile unit 30 moves in the circumferential direction, the guide portions 20 (21, 22) are also movable in the circumferential direction. For example, when the mobile unit 30 is moved in the circumferential direction at a predetermined velocity (angular velocity) V1, the guide portions 20 are movable in the circumferential direction at a predetermined velocity (angular velocity) V2 slower than the velocity V1. In this case, a relative velocity of the mobile unit 30 to the guide portions 20 is expressed by V1-V2. This makes it possible to decrease the relative velocity of the mobile unit 30 to the guide portions 20 compared with the case where the guide portions 20 are not moved in the circumferential direction (namely, in the case of V2=0). This reduces frictional resistance between the mobile unit 30 (the slide portions 32) and the guide portions 20 (21, 22), making it possible to further increase the durability of the guide portions 20. The above description is similarly applied to transport devices 2 to 4 described later.

Moreover, in the transport device 1, the cam mechanism 40 (the cam follower 35) is positioned closer to the center than the conductor 50 in the axial direction. Stated in another way, in the axial direction, a distance from a middle position C between the first guide portion 21 and the second guide portion 22 to the cam mechanism 40 is smaller than a distance from the middle position C to the conductor 50 (see FIG. 4). The axial-direction position of the cam mechanism 40 is assumed to be the position of the rotation center of the cam follower 35 in the radial direction of the cam follower 35 (namely, the position of the axial center of the transport-head connection shaft 34). The axial-direction position of the conductor 50 is assumed to be the position of the center of the conductor 50 in the axial direction.

In the cam mechanism 40, while the mobile unit 30 is moving in the circumferential direction, the cam follower 35 is moved following the cam groove 41, thus causing the transport head 33 to rotate about the axis of the radial direction. Because the transport head 33 includes the suction mechanism (not illustrated) as described above and has a certain magnitude of mass, inertial moment (inertia) generated with the operation of rotating the transport head 33 also tends to increase. In particular, if the distances from the cam mechanism 40 to the first guide portion 21 and the second guide portion 22 are different, a difference between forces acting on the first guide portion 21 and the second guide portion 22 tends to increase. In view of the above point, arranging the cam mechanism 40 as close as possible to the middle position C between the first guide portion 21 and the second guide portion 22 in the axial direction makes it easier to be evenly distribute the force generated with the rotation of the transport head 33 to the first guide portion 21 and the second guide portion 22. As a result, it is easier to further reduce the moment load acting on the guide portions 20. The above description is similarly applied to the transport devices 2 to 4 described later.

Second Embodiment

Figure 7:
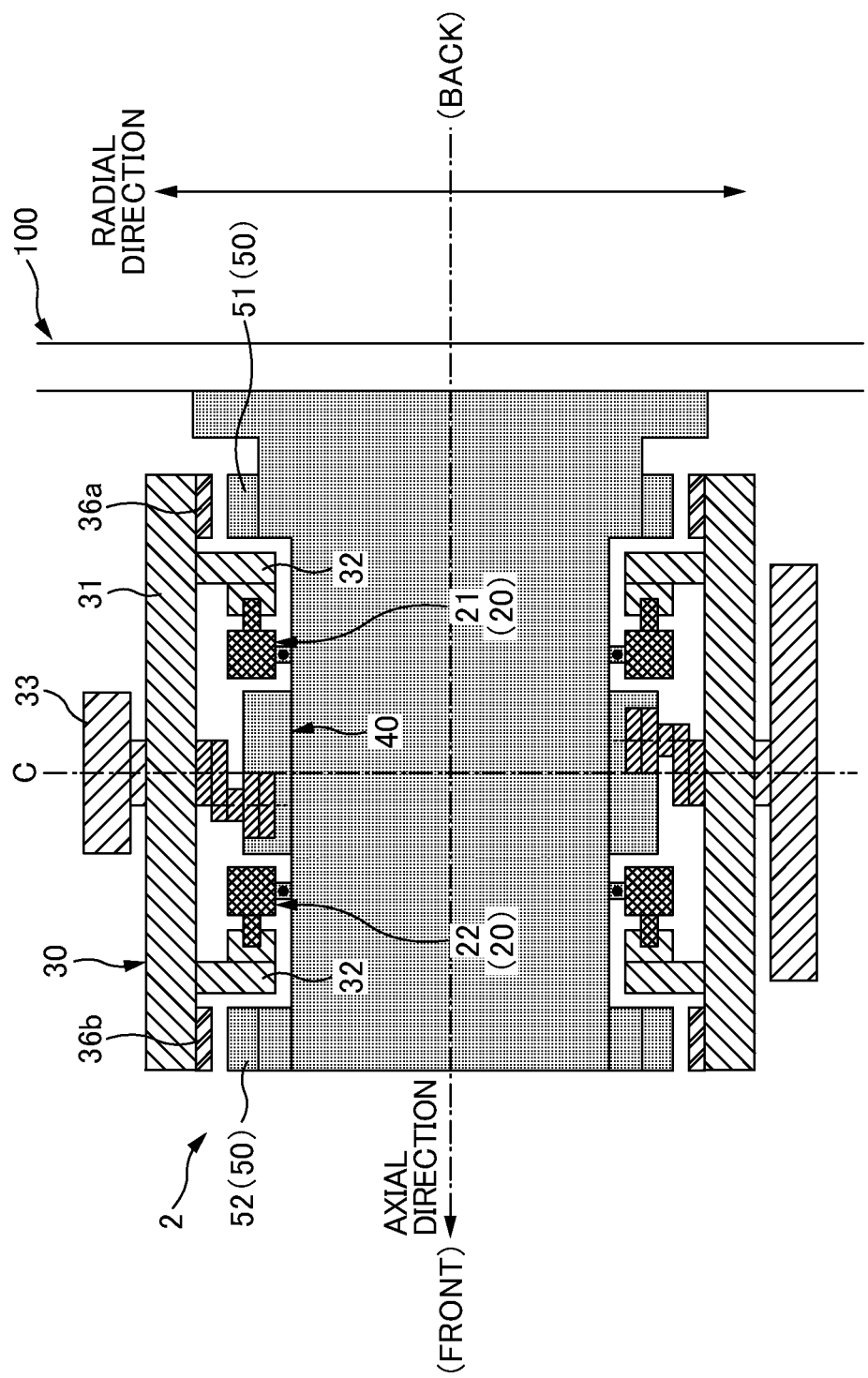
FIG. 7 is a schematic sectional view of a transport device 2 according to a second embodiment.

A second embodiment is described in connection with the transport device 2 in which the conductors 50 are disposed at each of two positions in the axial direction. FIG. 7 is a schematic sectional view of the transport device 2 according to the second embodiment. FIG. 7 corresponds to FIG. 4 illustrating the first embodiment.

In the transport device 2 illustrated in FIG. 7, in the axial direction, a first conductor 51 is disposed on the back side with respect to the first guide portion 21 and on the front side with respect to the wall 100, and a second conductor 52 is disposed on the front side with respect to the second guide portion 22. On the main body portion 31 of the mobile unit 30, a first magnet 36a is disposed at a position opposing the first conductor 51 in the radial direction, and a second magnet 36b is disposed at a position opposing the second conductor 52 in the radial direction. Components other than the conductor 50 and the magnet 36 are similar to those in the transport device 1 according to the first embodiment, and hence description of those components is omitted. Also in the transport device 2 according to the second embodiment, the moment loads acting on the pair of guide portions 21 and 22 can be reduced compared with those in the related-art transport device.

Figure 8:
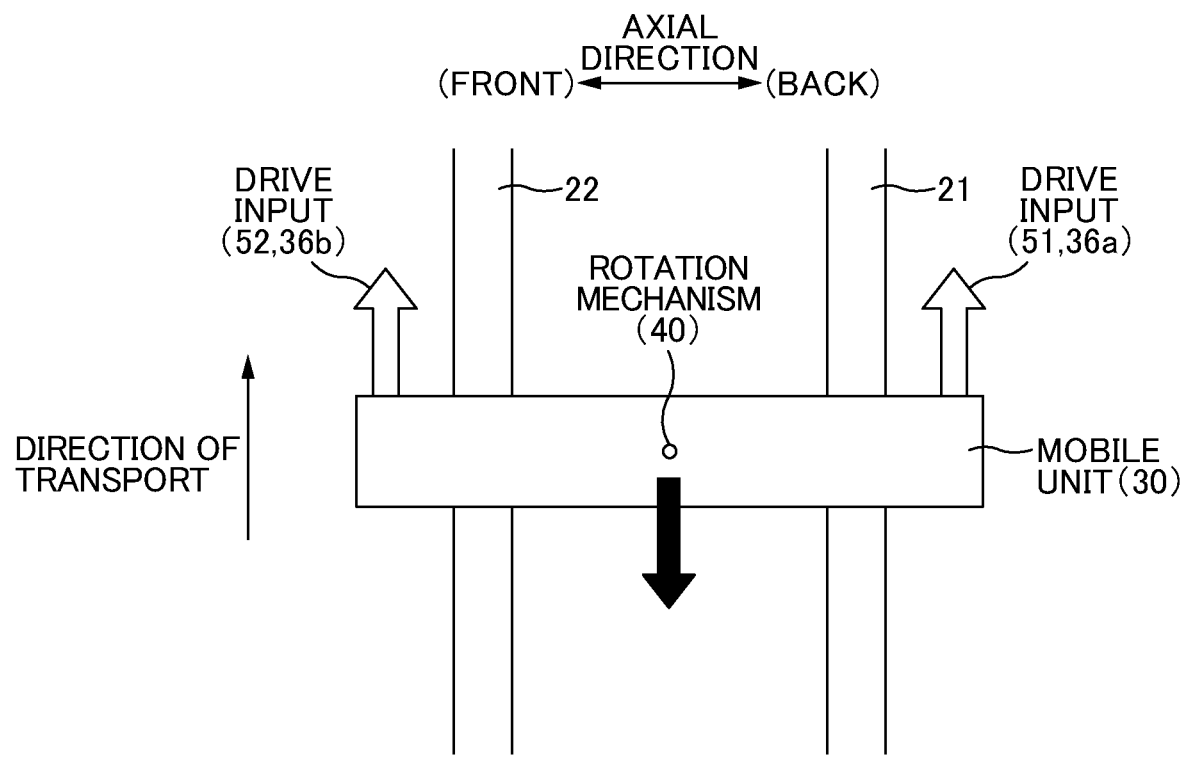
FIG. 8 is an explanatory view illustrating a relation between forces acting during transport in the transport device 2 according to the second embodiment.

FIG. 8 is an explanatory view illustrating a relation between forces acting during transport in the transport device 2 according to the second embodiment. In the transport device 2 according to the second embodiment, as illustrated in FIG. 8, the cam mechanism 40 for rotating the transport head 33 is disposed between the pair of guide portions 21 and 22 in the axial direction. On the other hand, the conductors 50 (51, 52) and the magnets 36 (36a, 36b) for inputting the driving force to move the mobile unit 30 are disposed on both the outer sides with respect to the pair of guide portions 20 (21, 22) in the axial direction. Accordingly, it is easier to make a propulsive force generated by the first conductor 51 and the first magnet 36a and a propulsive force generated by the second conductor 52 and the second magnet 36b evenly act on the mobile unit 30. In other words, the moments acting on the pair of guide portions 21 and 22 are more likely to become even. In addition, since the cam mechanism 40 is disposed near the middle position C between the pair of guide portions 21 and 22 in the axial direction, the force generated with the rotation of the transport head 33 is also more likely to evenly act on the pair of guide portions 21 and 22. As a result, the moment loads acting on the guide portions 20 can be further reduced more easily than in the case of using the related-art transport device described above with reference to FIG. 6A.

Particularly, in the transport device 2, the driving force to drive the mobile unit 30 is obtained through the propulsive force generated between the conductor 50 and the magnet 36 (based on the so-called linear servo control). In other words, a mechanism for rotating a rotor no longer needs to be disposed for each mobile unit unlike the related art using a servomotor, and operations of the multiple mobile units can be controlled collectively by controlling the currents supplied to the conductors 50 that are disposed on the transport path. Accordingly, drive input can be performed even with a small space and, as illustrated in FIG. 7, the driving force can be input to the mobile unit 30 even using a narrow space between the wall 100 and the first guide portion 21. As a result, the durability of the guide portions 20 is increased, and the mobile unit 30 can more stably perform the transport operation.

Third Embodiment

Figure 9A:
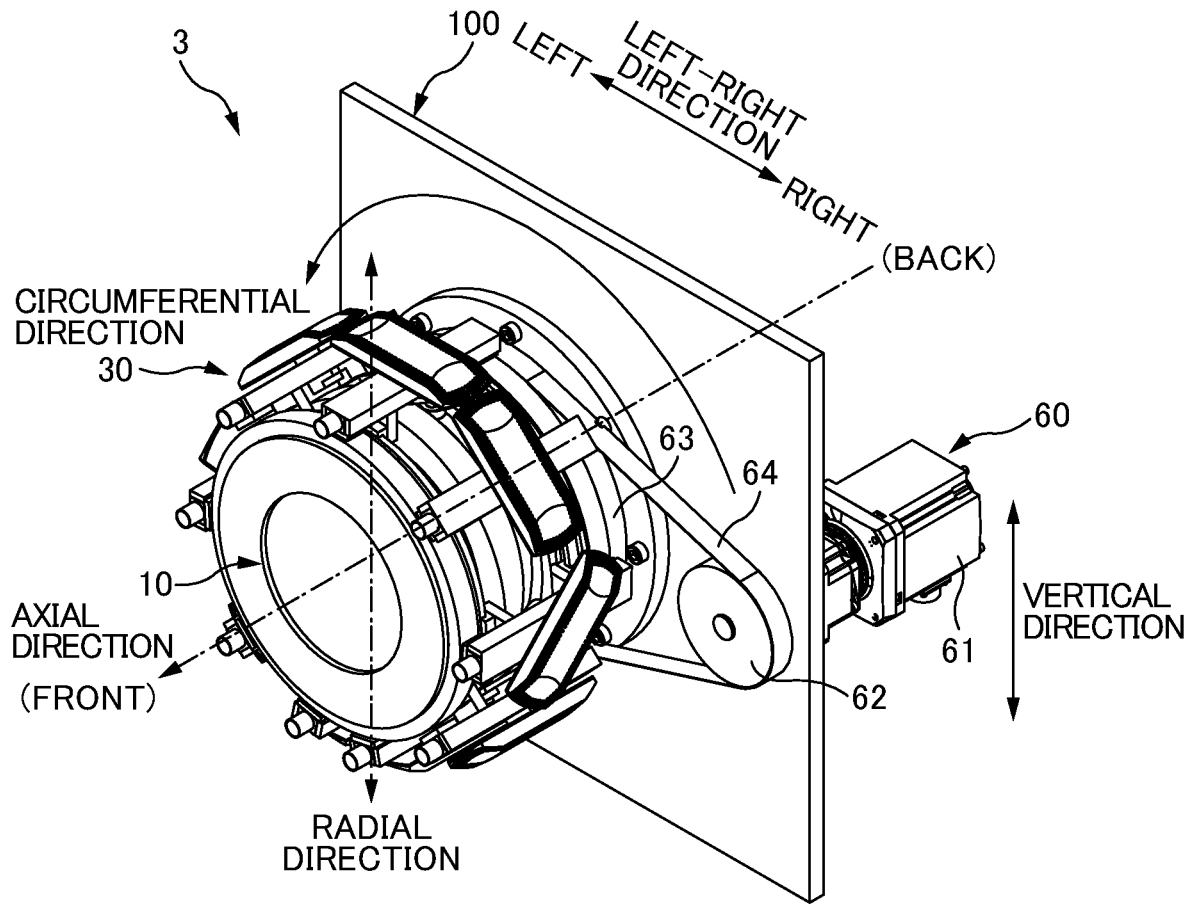
FIG. 9A is a perspective view illustrating an entire structure of an example of a transport device 3 according to a third embodiment.
Figure 9B:
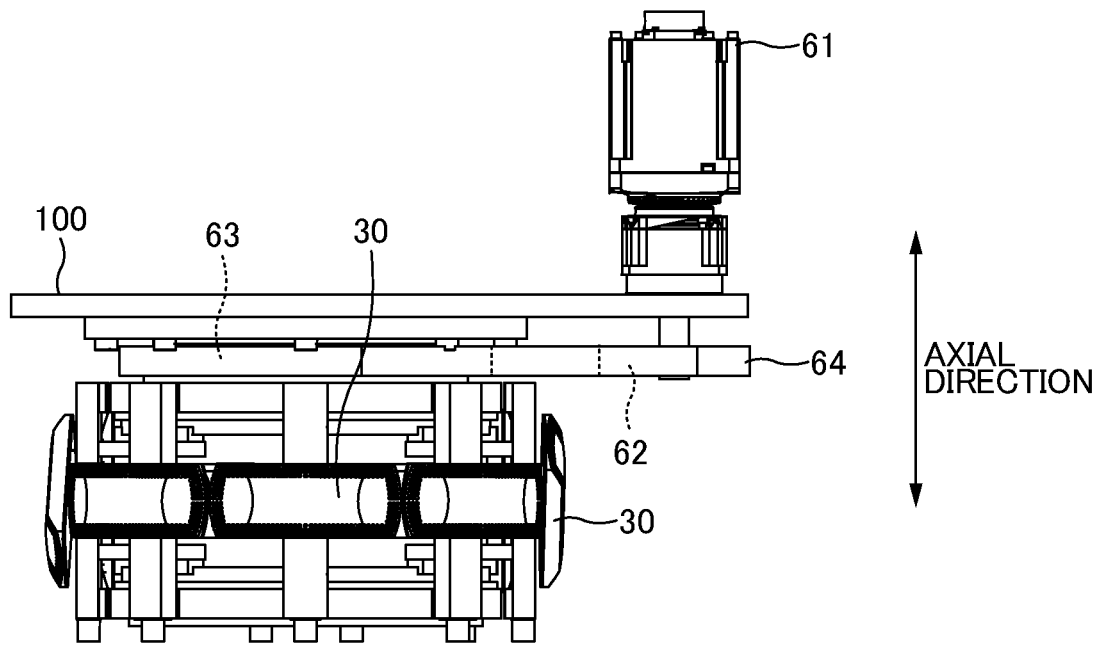
FIG. 9B illustrates a state of the transport device 3 illustrated in FIG. 9A when viewed from the upper side in a vertical direction.
Figure 10:
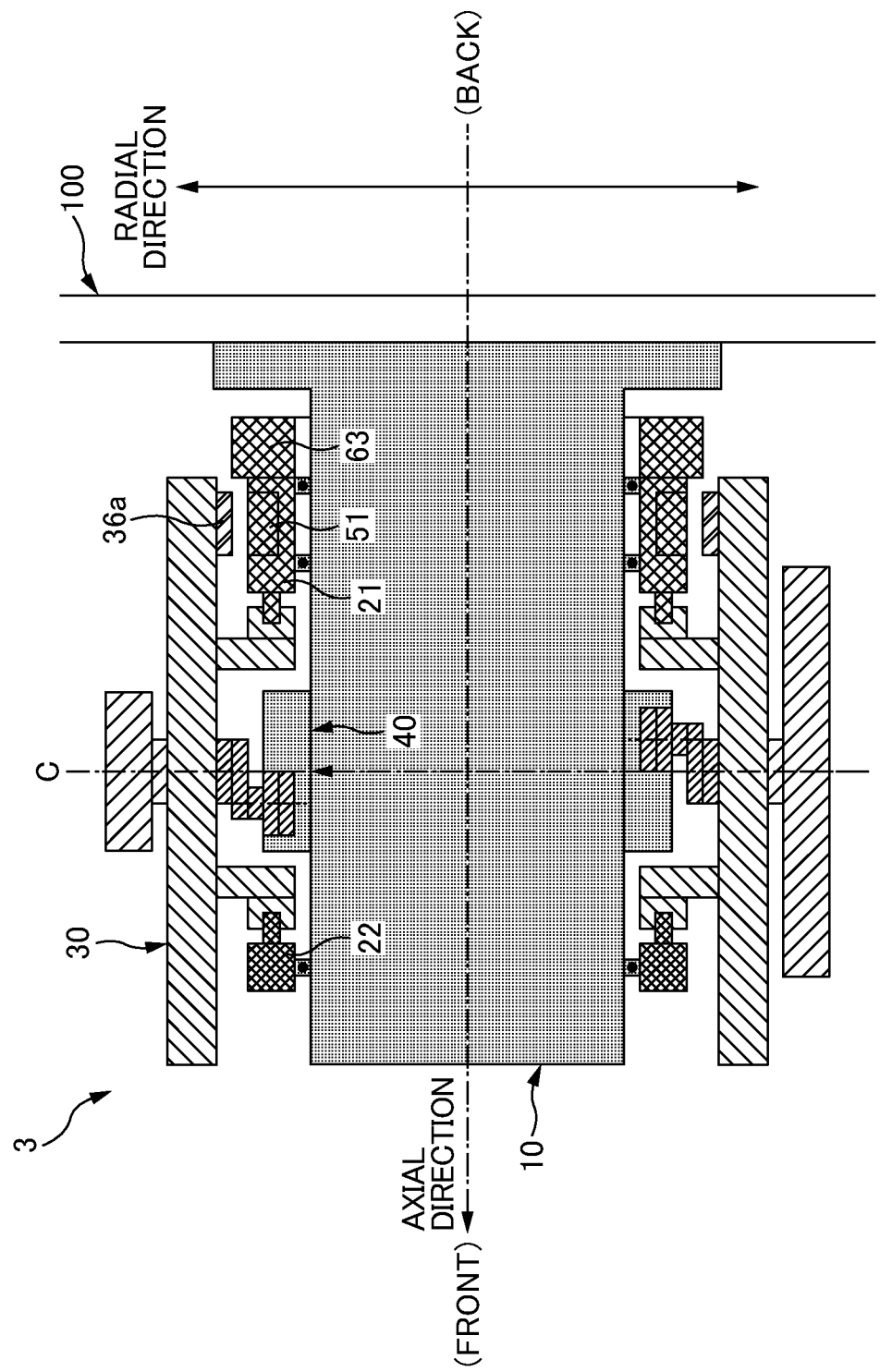
FIG. 10 is schematic sectional view of the transport device 3.

A third embodiment is described in connection with the transport device 3 in which the conductor 50 is driven to rotate in the circumferential direction. FIG. 9A is a perspective view illustrating an entire structure of an example of the transport device 3 according to the third embodiment, and FIG. 9B illustrates a state of the transport device 3 illustrated in FIG. 9A when viewed from the upper side in a vertical direction. FIG. 10 is a schematic sectional view of the transport device 3.

In addition to the structure of the transport device 1 according to the first embodiment or the transport device 2 according to the second embodiment, the transport device 3 includes a conductor drive unit 60 for driving the conductor 50 to rotate in the circumferential direction. The conductor drive unit 60 includes a drive motor 61, a drive output pulley 62, a drive input pulley 63, and a power transmission belt 64. The drive motor 61 is fixed on the back side in the axial direction with respect to the wall 100 and generates a driving force to drive and rotate the conductor 50. The drive output pulley 62 is a disk-shaped member disposed on the front side in the axial direction with respect to the wall 100 and is coupled to an output shaft of the drive motor 61. The drive output pulley 62 is rotated with rotation of the drive motor 61, thereby outputting torque. The drive input pulley 63 is a ring-shaped member positioned concentric with the shaft portion 10 on the front side in the axial direction with respect to the wall 100, and is disposed on the outer circumferential surface of the shaft portion 10. The power transmission belt 64 is stretched to run over outer circumferential surfaces of the drive output pulley 62 and the drive input pulley 63, and to input the torque output from the drive output pulley 62 to the drive input pulley 63. As a result, the drive input pulley 63 can be rotated in the circumferential direction over the outer circumferential surface of the shaft portion 10 at a predetermined angular velocity.

Furthermore, in the transport device 3 illustrated in FIG. 10, the first conductor 51 is not fixed to the outer circumferential surface of the shaft portion 10, and can move rotationally in the circumferential direction. More specifically, the first conductor 51 is coupled integrally with both of the drive input pulley 63 and the first guide portion 21 and is disposed on the outer circumferential surface of the shaft portion 10 with the ball bearings 25 interposed therebetween. Accordingly, with rotation of the drive input pulley 63, the first conductor 51 is driven to rotate together with the first guide portion 21 in the circumferential direction at the predetermined angular velocity.

Because the first conductor 51 is driven and rotated, a relative velocity (angular velocity) of the mobile unit 30 to the first conductor 51 can be made slower than when the first conductor 51 is held stationary. It is assumed that the movement velocity (angular velocity) of the mobile unit 30 in the circumferential direction relative to the shaft portion 10 is V1. In this case, when the first conductor 51 is for example held stationary as in the transport device 2, the relative velocity of the mobile unit 30 to the first conductor 51 also needs to be V1. On the other hand, when the first conductor 51 is moved in the circumferential direction at a movement velocity (angular velocity) V3, the relative velocity of the mobile unit 30 to the first conductor 51 is given by V1-V3. Accordingly, the relative velocity of the mobile unit 30 to the first conductor 51 can decrease by a value corresponding to the movement velocity V3 of the first conductor 51. This makes easier control by the control unit 70, making it possible to more easily stabilize the operation of moving the mobile unit 30 by the linear motor.

Moreover, in the transport device 3, the first guide portion 21 is further movable in the circumferential direction together with the first conductor 51. Hence the relative velocity of the mobile unit 30 to the guide portion 20 can also be made lower than when the guide portion 20 (the first guide portion 21) is not moved in the circumferential direction. As a result, frictional resistance between the mobile unit 30 and the guide portion 20 is reduced, and the durability of the guide portion 20 can be further increased. In other words, the transport device 3 can increase the durability of the guide portion 20 while easily stabilizing the operation of moving the mobile unit 30.

In the example of FIG. 10, concerning the first guide portion 21 being one of the pair of guide portions 21 and 22 which is positioned closer to the wall 100, the drive input pulley 63 is disposed in a space between the first guide portion 21 and the wall 100 in the axial direction, and the drive input pulley 63 serves as a drive mechanism for driving and rotating the conductor 50 (the first conductor 51) and the guide portion 20 (the first guide portion 21). Accordingly, the first guide portion 21 can be driven and rotated together with the first conductor 51 by the disk-shaped drive input pulley 63, and therefore the drive mechanism can be installed even in the narrow space between the wall 100 and the first guide portion 21.

In trying to drive and rotate the guide portion in the related-art transport device, there are both required separately a drive input unit (for example, a motor) for driving and rotating the mobile unit and a drive input unit (for example, a motor) for driving and rotating the guide portion. This increases the size of the drive mechanism, making it difficult to install the drive mechanism between the wall 100 and the first guide portion 21 positioned closer to the wall 100. In contrast, in the transport device 3, since the mobile unit 30 is driven and rotated with supply of the current to the conductor 50 based on the linear servo control, there is no need to install a motor and so on for driving and rotating at least the mobile unit 30. Accordingly, the drive mechanism (the drive input pulley 63) can be disposed in the narrow space between the wall 100 and the first guide portion 21. The drive mechanism can drive and rotate the first guide portion 21, also making it possible to simultaneously perform input of the driving force (supply of the current to the conductor 50) to drive and rotate the mobile unit 30. It is hence possible to form the entirety of the transport device 3 in a compact size, and to increase the degree of freedom in design while minimizing a space for installation of the transport mechanism.

Figure 11:
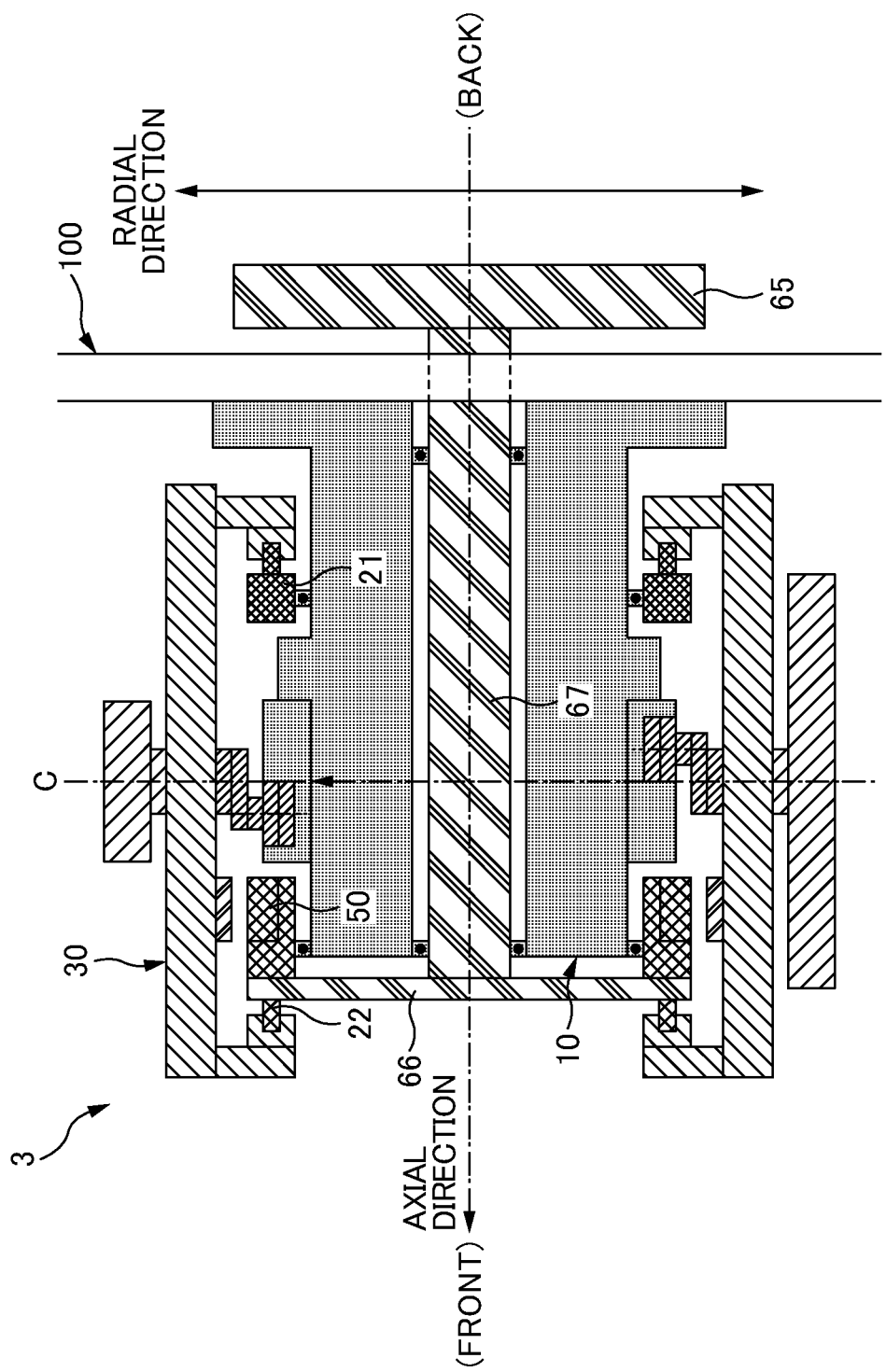
FIG. 11 is a schematic sectional view of a modification of the transport device 3.

While the transport device 3 illustrated in FIG. 10 is configured to drive and to rotate the first conductor 51 and the first guide portion 21 in the circumferential direction on the back side in the axial direction, the transport device 3 may be configured to drive and to rotate the second conductor 52 and the second guide portion 22 in the circumferential direction on the front side in the axial direction. FIG. 11 is a schematic sectional view of a modification of the transport device 3.

The transport device 3 illustrated in FIG. 11 is different from the transport device 3 illustrated in FIG. 10 in terms of the structure of the drive input pulley. More specifically, a drive input pulley 65, a power transmission disk 66, and a connection shaft 67 are disposed instead of the drive input pulley 63 in FIG. 10, driving and rotating the second conductor 52 and the second guide portion 22 in the circumferential direction.

In more detail, as illustrated in FIG. 11, the drive input pulley 65 is a disk-shaped member that is positioned concentric with the shaft portion 10 on the back side with respect to the wall 100 in the axial direction. Furthermore, in this modification, the drive output pulley 62 (not illustrated in FIG. 11) is disposed on the back side with respect to the wall 100 in the axial direction. The torque output from the drive output pulley 62 is input to the drive input pulley 65 through the power transmission belt 64. The power transmission disk 66 is a disk-shaped member that is disposed concentric with the shaft portion 10 in front of a front-side end of the shaft portion 10 in the axial direction. Moreover, the shaft portion 10 in this modification has a cylindrical shape, and the connection shaft 67 extending in the axial direction is disposed in a cylindrical inner (hollow) space of the shaft portion 10 to be rotatable in the circumferential direction. A back-side end of the connection shaft 67 in the axial direction is connected to the drive input pulley 65, and a front-side end of the connection shaft 67 in the axial direction is connected to the power transmission disk 66. In other words, the drive input pulley 65 and the power transmission disk 66 are formed into an integral unit with the connection shaft 67 interposed therebetween and are rotatable in the circumferential direction with the connection shaft 67 serving as a rotation shaft.

As illustrated in FIG. 11, the power transmission disk 66 is coupled to the conductor 50 and the guide portion 20 (the second guide portion 22). Accordingly, when the torque generated by the drive motor 61 is input from the drive output pulley 62 to the drive input pulley 65 through the power transmission belt 64, the drive input pulley 65 and the power transmission disk 66 are integrally driven to rotate in the circumferential direction, whereby the conductor 50 and the second guide portion 22 both coupled to the power transmission disk 66 are also driven to rotate in the circumferential direction. Hence, as in the case of FIG. 10, the relative velocity (angular velocity) of the mobile unit 30 to the conductor 50 can be reduced and the operation of moving the mobile unit 30 can be stabilized more easily. In addition, the relative velocity of the mobile unit 30 to the non-magnetic layer 20 (the second guide portion 22) is also reduced. As a result, the frictional resistance between the mobile unit 30 and the guide portions 20 is reduced, and the durability of the guide portions 20 can be further increased.

In the transport device 3 according to the third embodiment, one of the pair of guide portions 21 and 22 is driven to rotate together with the conductor in the circumferential direction, but the other guide portion can freely move rotationally in the circumferential direction without being driven to rotate. In the transport device illustrated in FIG. 11, for example, the second guide portion 22 located on the front side in the axial direction is driven to rotate in the circumferential direction, whereas the first guide portion 21 located on the back side in the axial direction is not driven and is freely rotatable in the circumferential direction. Accordingly, the control unit 70 is just required to control the operation of rotating only one of the pair of guide portions 21 and 22, and is no longer required to control the rotational operation of the other guide portion. As a result, control of the transport operation by the transport device 3 can be facilitated.

Fourth Embodiment

Figure 12:
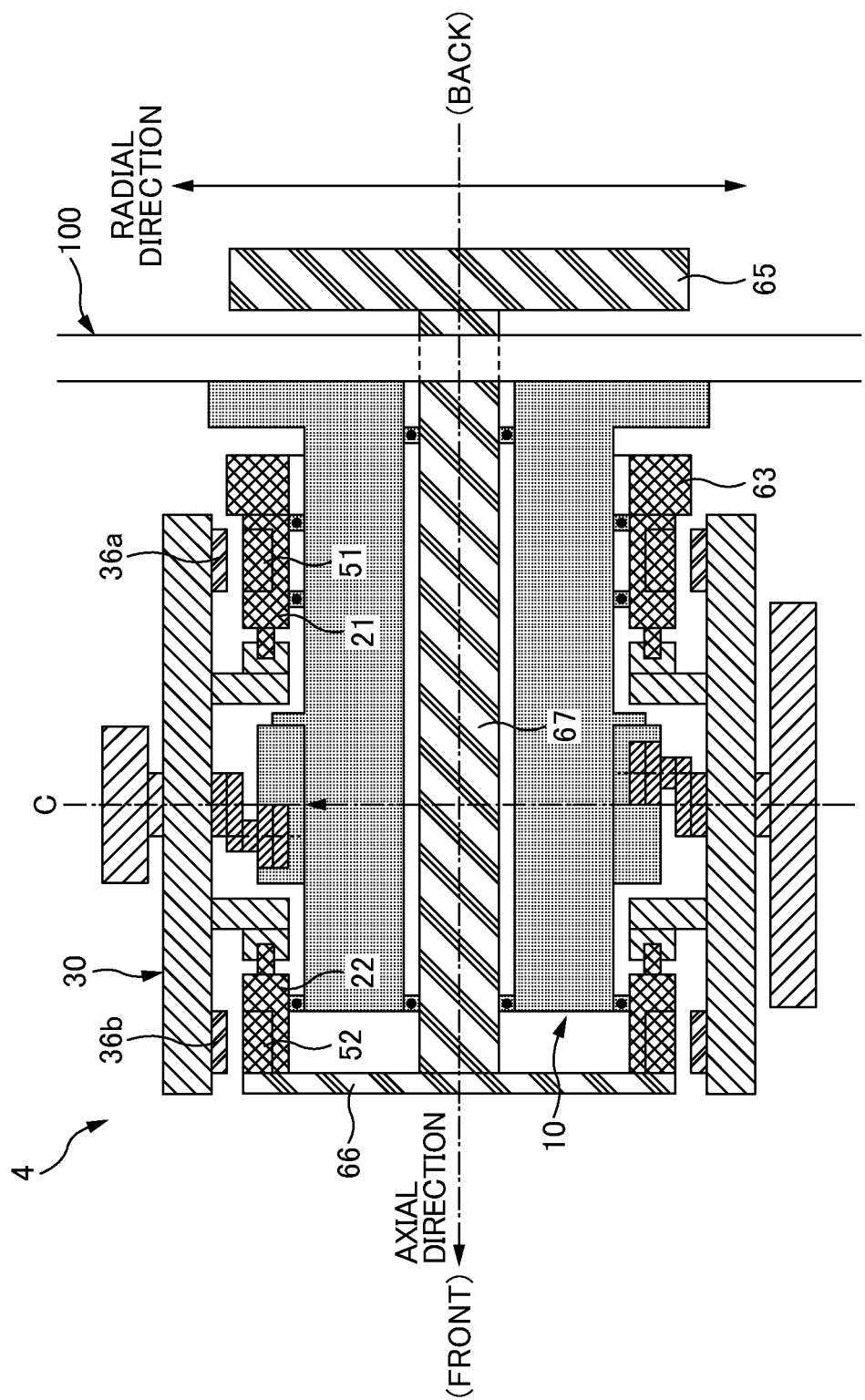
FIG. 12 is schematic sectional view of a transport device 4 according to a fourth embodiment.

A fourth embodiment is described in connection with a transport device 4 in which the pair of guide portions 21 and 22 are both driven to rotate in the circumferential direction. FIG. 12 is a schematic sectional view of the transport device 4.

The transport device 4 according to the fourth embodiment includes the conductor drive unit 60 as in the transport device 3 according to the third embodiment and drives the pair of guide portions 21 and 22 and the pair of conductors 51 and 52 by the conductor drive unit 60. More specifically, the conductor drive unit 60 includes the drive motor 61, the drive output pulley 62, a first drive input pulley 63, the power transmission belt 64, a second drive input pulley 65, the power transmission disk 66, and the connection shaft 67. In addition, the drive output pulley 62 in the transport device 4 is constituted by a first drive output pulley 62a (not illustrated) disposed on the front side with respect to the wall 100 in the axial direction and outputting torque to the first drive input pulley 63, and by a second drive output pulley 62b (not illustrated) disposed on the back side with respect to the wall 100 in the axial direction and outputting torque to the second drive input pulley 65. The power transmission belt 64 is constituted by a first power transmission belt 64a (not illustrated) for transmitting the torque from the first drive output pulley 62a to the first drive input pulley 63 and a second power transmission belt 64b (not illustrated) for transmitting the torque from the second drive output pulley 62b to the second drive input pulley 65.

When the transport operation is performed by the transport device 4, the torque generated by the drive motor 61 is input to the first drive input pulley 63 to rotate the first drive input pulley 63 in the circumferential direction at a predetermined angular velocity, whereby the first conductor 51 and the first guide portion 21 both coupled integrally with the first drive input pulley 63 are driven to rotate in the circumferential direction at the predetermined angular velocity. Similarly, the torque generated by the drive motor 61 is input to the second drive input pulley 65 to rotate the second drive input pulley 65 in the circumferential direction at the predetermined angular velocity, whereby the power transmission disk 66 (and the connection shaft 67) is rotated and both of the second conductor 52 and the second guide portion 22 coupled integrally with the power transmission disk 66 are driven to rotate in the circumferential direction at the predetermined angular velocity.

Since the pair of guide portions 21 and 22 are both driven and rotated, the frictional resistance between each of the guide portions and the mobile unit 30 can be further reduced. Furthermore, since the pair of the conductors 51 and 52 are also driven and rotated together with the guide portions, the operation of the mobile unit 30 can be stabilized more easily.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A linear-motor type transport device for transporting material for an absorbent article comprising:
   a shaft portion that has an axial direction, a radial direction, and a circumferential direction, wherein the axial direction extends horizontally from a vertically erected wall that supports the shaft portion;
   a pair of guide portions that is disposed on the shaft portion with a predetermined axial-direction space between the guide portions and that forms an orbital transport path that extends along the circumferential direction;
   a mobile unit that moves on the transport path along the guide portions while supporting a transport head rotatably about a rotation axis, wherein
      the rotation axis extends along the radial direction, and
      the transport head transports a material for an absorbent article;
   a cam mechanism that rotates the transport head about the rotation axis through a predetermined angle when the mobile unit is moved on the transport path; and
   a controller that moves the mobile unit by supplying currents to conductors and generating a propulsive force between one of the conductors and a magnet that is disposed on the mobile unit, wherein
      the conductors are disposed along the transport path, and
      the cam mechanism and the magnet are disposed between the guide portions in the axial direction, wherein
   the conductors are driven to rotate in the circumferential direction.

2. The linear-motor type transport device according to claim 1, wherein the guide portions move rotationally in the circumferential direction.

3. The linear-motor type transport device according to claim 1, wherein the conductors are driven to rotate in the circumferential direction together with at least one of the guide portions.

4. The linear-motor type transport device according to claim 3, wherein
   the guide portions include a first guide portion and a second guide portion, the linear-motor type transport device further comprises a drive mechanism disposed between the first guide portion and the wall, the first guide portion is disposed on one side in the axial direction with respect to the wall, the second guide portion is disposed on the one side in the axial direction with respect to the first guide portion, and the drive mechanism drives and rotates the conductors and the guide portions.

5. The linear-motor type transport device according to claim 3, wherein the guide portions include a first guide portion and a second guide portion, the first guide portion is driven to rotate in the circumferential direction together with the conductors, and the second guide portion is freely moving rotationally in the circumferential direction.

6. The linear-motor type transport device according to claim 3, wherein both of the guide portions are driven to rotate in the circumferential direction together with the conductors.

7. The linear-motor type transport device according to claim 1, wherein in the axial direction, a distance from a middle position between the guide portions to the cam mechanism is smaller than a distance from the middle position to one of the conductors.

8. A method for manufacturing an absorbent article using a material for an absorbent article, wherein the material is transported in a direction of transport by the linear-motor type transport device according to claim 1.

9. A linear-motor type transport device for transporting material for an absorbent article comprising:

a shaft portion that has an axial direction, a radial direction, and a circumferential direction, wherein the axial direction extends horizontally from a vertically erected wall that supports the shaft portion;

a pair of guide portions that is disposed on the shaft portion with a predetermined axial-direction space between the guide portions and that forms an orbital transport path that extends along the circumferential direction;

a mobile unit that moves on the transport path along the guide portions while supporting a transport head rotatably about a rotation axis, wherein the rotation axis extends along the radial direction, and the transport head transports a material for an absorbent article;

a cam mechanism that rotates the transport head about the rotation axis through a predetermined angle when the mobile unit is moved on the transport path; and a controller that moves the mobile unit by supplying currents to conductors and generating a propulsive force between one of the conductors and a magnet that is disposed on the mobile unit, wherein the conductors are disposed along the transport path, the guide portions include a first guide portion and a second guide portion, the first guide portion is disposed on a first side in the axial direction with respect to the wall, the second guide portion is disposed on the first side in the axial direction with respect to the first guide portion, the cam mechanism, in the axial direction, is disposed between the first guide portion and the second guide portion, the magnet comprises a first magnet and a second magnet, the first magnet is disposed on the first side in the axial direction with respect to the wall and on a second side in the axial direction with respect to the first guide portion, the second magnet is disposed on the first side in the axial direction with respect to the second guide portion, and the conductors are driven to rotate in the circumferential direction.

* * * * *